United States Patent
Samsonova et al.

(10) Patent No.: US 9,029,104 B2
(45) Date of Patent: May 12, 2015

(54) METHOD FOR PRODUCING AN L-AMINO ACID BELONGING TO THE GLUTAMATE FAMILY, USING A CORYNEFORM BACTERIUM

(71) Applicant: Ajinomoto Co., Inc., Tokyo (JP)

(72) Inventors: Svetlana Alekseevna Samsonova, Moscow (RU); Viktor Vasilievich Samsonov, Moscow (RU); Yulia Georgievna Rostova, Moscow (RU); Mikhail Markovich Gusyatiner, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 14/045,205

(22) Filed: Oct. 3, 2013

(65) Prior Publication Data

US 2014/0051132 A1  Feb. 20, 2014

Related U.S. Application Data

(63) Continuation of application No. PCT/JP2012/061625, filed on Apr. 25, 2012.

(30) Foreign Application Priority Data

Apr. 25, 2011  (RU) .............................. 2011116147

(51) Int. Cl.
| | | |
|---|---|---|
| C12P 13/14 | (2006.01) |
| C12P 13/24 | (2006.01) |
| C12N 1/20 | (2006.01) |
| C12N 15/00 | (2006.01) |
| C07H 21/04 | (2006.01) |
| C07K 14/34 | (2006.01) |
| C12P 13/10 | (2006.01) |

(52) U.S. Cl.
CPC ................. *C12P 13/14* (2013.01); *C07K 14/34* (2013.01); *C12P 13/10* (2013.01); *C12P 13/24* (2013.01)

(58) Field of Classification Search
None
See application file for complete search history.

(56) References Cited

U.S. PATENT DOCUMENTS

| 4,278,765 A | 7/1981 | Debabov et al. |
| 4,346,170 A | 8/1982 | Sano et al. |
| 5,661,012 A | 8/1997 | Sano et al. |
| 6,040,160 A | 3/2000 | Kojima et al. |
| 2007/0020257 A1 | 1/2007 | Nishizawa |

FOREIGN PATENT DOCUMENTS

| EP | 2248906 A1 | 11/2010 |
| WO | WO95/16042 A1 | 6/1995 |

OTHER PUBLICATIONS

Schreier H. J., et al., "Regulation of *Bacillus subtilis* Glutamine Synthetase Gene Expression by the Product of the glnR Gene," J. Mol. Biol. 1989;210:51-63.

*Primary Examiner* — Christian Fronda
(74) *Attorney, Agent, or Firm* — Shelly Guest Cermak; Cermak Nakajima & McGowan LLP (57) ABSTRACT

The present invention provides a method for producing an L-amino acid belonging to the glutamate family, using a coryneform bacterium which has been modified so that expression of one or more gene(s) of the NCgl_2067-NCgl_2065 operon in said bacterium is/are attenuated.

21 Claims, 2 Drawing Sheets

Fig. 1

```
spr0443    15   IGSVMKLTDLSARQIRYYEDQELIKPDRNEGNRRMYSLNDMDRLLEIKDYISEGYNIA--   72
                IG V KL+ +SAR +R+YE    L++P ++    R YS  D+ R+  I+   S G ++
NCgl2066    3   IGEVSKLSGVSARMLRHYEKLGLVEPKQSTAGYREYSEGDVRRIFHIEGLRSLGLSLKQV   62 spr0443    73   --AIKKKYAEREAKSKKAVSQTEVRRALHNELL   103
                  A++    + +A   + +++T  R ++  ELL
NCgl2066   63   GDALEDPDFDPQAVISEMIAETSARISMERELL   95
```

METHOD FOR PRODUCING AN L-AMINO ACID BELONGING TO THE GLUTAMATE FAMILY, USING A CORYNEFORM BACTERIUM

This application is a Continuation of, and claims priority under 35 U.S.C. §120 to, International Application No. PCT/JP2012/061625, filed Apr. 25, 2012, and claims priority therethrough under 35 U.S.C. §119 to Russian Patent Application No. 2011116147, filed Apr. 25, 2011, the entireties of which are incorporated by reference herein. Also, the Sequence Listing filed electronically herewith is hereby incorporated by reference (File name: 2013-10-03T_US-463_Seq_List; File size: 22 KB; Date recorded: Oct. 3, 2013).

BACKGROUND OF THE INVENTION

1. Field of the Invention

The present invention relates to the microbiological industry, and specifically to a method for producing an L-amino acid belonging to the glutamate family using a coryneform bacterium which has been modified so that expression of one or more gene(s) of the NCgl_2067-NCgl_2065 operon in the bacterium is/are attenuated.

2. Brief Description of the Related Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance L-amino acid production yields have been reported, including by transforming microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition by the resulting L-amino acid (see, for example, WO 95/16042 or U.S. Pat. Nos. 4,346,170; 5,661,012 and 6,040,160).

Many methods for producing L-glutamine by culturing a coryneform bacterium have been disclosed. For example, EP1229121 A2 discloses a method for producing L-glutamine by culturing a coryneform bacterium which has L-glutamine producing ability and has been modified so that its intracellular glutamine synthetase activity is enhanced, and preferably has been further modified so that its intracellular glutamate dehydrogenase activity is enhanced, in a medium to produce and cause accumulation of L-glutamine in the medium, and collecting the L-glutamine.

It is known that transcription of the *Bacillus subtilis* gene encoding glutamine synthetase (glnA) is regulated by the nitrogen source. The glnA gene is located in an operon with the glnR gene. The glnR gene codes for a negative regulator which directly controls expression of the glutamine synthetase gene (glnA). Certain mutations in glnR gene, such as a large, in-frame deletion and a start codon mutation, lead to high-level constitutivity of the operon; whereas other mutations caused low-level constitutivity (Schreier H J et al., J Mol. Biol. 1989, 210(1): 51-63).

Recently, regulation of glutamine and glutamate metabolism by the nitrogen regulatory protein GlnR in *Streptococcus pneumoniae* was analyzed. Using DNA microarray analyses of *S. pneumoniae* D39 wild-type and its isogenic glnR mutant which had been grown in nitrogen-rich medium supplemented with glutamine, a list of operons and genes that were up-regulated the most in the glnR mutant was determined, and includes the following genes: glnA (encoding glutamine synthetase GlnA), glnPQ (encoding ABC transporter amino acid-binding protein/permease), and gdhA (encoding glutamate dehydrogenase glutamate dehydrogenase). All of these genes have a GlnR operator in their promoter regions. Also the zwf gene, encoding the glucose-6-phosphate dehydrogenase and located downstream of, and in the same orientation as glnPQ, was up-regulated (Kloosterman et al., J Biol. Chem. 2006, 281(35):25097-25109). Currently, there have been no reports about the presence of the putative glnR gene in the genomes of coryneform bacteria.

There have been no reports of attenuating expression of one or more genes of the NCgl_2067-NCgl_2065 operon for the purpose of improving productivity of L-amino acid belonging to the glutamate family.

SUMMARY OF THE INVENTION

Aspects of the present invention include enhancing the productivity of strains which produce L-amino acids belonging to the glutamate family, and providing a method for producing an L-amino acid belonging to the glutamate family, using these strains.

An open reading frame, (ORF) NCgl_2066, was found in the genome of *Corynebacterium glutamicum* which is homologous to the glnR gene from *Streptococcus pneumoniae*. The ORF NCgl_2066 is located in an operon with two other ORFs—NCgl_2067 and NCgl_2065. The corresponding ORFs were named NCgl_2067, NCgl_2066, and NCgl_2065 genes, and the operon was given the name NCgl_2067-NCgl_2065 operon.

The above aspects were achieved by finding that attenuation of the expression of one or more gene(s) of the NCgl_2067-NCgl_2065 operon can enhance production of L-amino acids belonging to the glutamate family, such as L-glutamic acid, L-glutamine, L-proline, L-histidine, L-arginine, L-ornithine, and L-citrulline.

The present invention provides a coryneform bacterium having an increased ability to produce amino acids belonging to the glutamate family, such as L-glutamic acid, L-glutamine, L-proline, L-histidine, L-arginine, L-ornithine, L-citrulline, and combinations thereof.

It is an aspect of the present invention to provide a coryneform bacterium which is able to produce an L-amino acid belonging to the glutamate family, wherein said bacterium has been modified so that the expression of one or more gene(s) of the NCgl_2067-NCgl_2065 operon in said bacterium is attenuated.

It is a further aspect of the present invention to provide the bacterium as described above, wherein said bacterium has been modified to attenuate the expression of the NCgl_2067 gene.

It is a further aspect of the present invention to provide the bacterium as described above, wherein said expression of the NCgl_2067 gene is attenuated by inactivation of the NCgl_2067 gene.

It is a further aspect of the present invention to provide the bacterium as described above, wherein said bacterium has been modified to attenuate the expression of the NCgl_2066 gene.

It is a further aspect of the present invention to provide the bacterium as described above, wherein said expression of the NCgl_2066 gene is attenuated by inactivation of the NCgl_2066 gene.

It is a further aspect of the present invention to provide the bacterium as described above, wherein said bacterium belongs to genus *Corynebacterium* or *Brevibacterium*.

It is a further aspect of the present invention to provide the bacterium as described above, wherein said bacterium is *Brevibacterium flavum*.

It is a further aspect of the present invention to provide the bacterium as described above, wherein said L-amino acid belonging to the glutamate family is selected from the group consisting of L-glutamic acid, L-glutamine, L-proline, L-histidine, L-arginine, L-ornithine, L-citrulline, and combinations thereof.

It is a further aspect of the present invention to provide the bacterium as described above, wherein said L-amino acid is selected from the group consisting of L-glutamic acid and L-glutamine.

It is a further aspect of the present invention to provide a method for producing an L-amino acid belonging to the glutamate family comprising:

cultivating the bacterium as described above in a medium, and collecting said L-amino acid from the medium.

It is a further aspect of the present invention to provide the method as described above, wherein said L-amino acid belonging to the glutamate family is selected from the group consisting of L-glutamic acid, L-glutamine, L-proline, L-histidine, L-arginine, L-ornithine, L-citrulline, and combinations thereof.

It is a further aspect of the present invention to provide the method as described above, wherein said L-amino acid is selected from the group consisting of L-glutamic acid and L-glutamine.

The present invention is described in detail below.

DESCRIPTION OF THE PREFERRED EMBODIMENTS

The present invention is described in detail below.
1. Bacterium of the Present Invention A coryneform bacterium is described which can produce an L-amino acid belonging to the glutamate family, wherein the bacterium has been modified to attenuate expression of one or more gene(s) of the NCgl_2067-NCgl_2065 operon.

The phrase "bacterium producing an L-amino acid" can mean a bacterium which has an ability to produce and excrete an L-amino acid into a medium, when the bacterium is cultured in the medium.

The phrase "bacterium producing an L-amino acid" as used herein also can mean a bacterium which is able to produce and cause accumulation of an L-amino acid in a culture medium in an amount larger than a wild-type or parental strain of coryneform bacterium, for example, bacterial strains listed below, such as *Corynebacterium glutamicum* ATCC 13032, ATCC 31833, *Brevibacterium flavum* ATCC 13826, ATCC 14067, AJ12418 and B-6642, and can mean that the microorganism is able to cause accumulation in a medium of an amount not less than 0.5 g/l, or 1.0 g/l, of the target L-amino acid.

The phrase "L-amino acid belonging to the glutamate family" can include L-glutamic acid, L-glutamine, L-proline, L-histidine, L-arginine, L-ornithine, L-citrulline, and combinations thereof.

The term "coryneform bacteria" can include conventional coryneform bacterium according to the classification known to a person skilled in the art of microbiology, and also can include bacteria that had been classified into the genus *Brevibacterium*, but are currently classified into the genus *Corynebacterium*(Liebl W et al., Int J Syst Bacteriol. 1991, 41(2): 255-260), as well as the *Brevibacterium* bacteria that are highly related to *Corynebacterium* bacteria. Examples of such coryneform bacterium include the following:

*Corynebacterium acetoacidophilum*
*Corynebacterium acetoglutamicum*
*Corynebacterium alkanolyticum*
*Corynebacterium callunae*
*Corynebacterium glutamicum* (*Micrococcus glutamicus*)
*Corynebacterium lilium*
*Corynebacterium melassecola*
*Corynebacterium thermoaminogenes* (*Corynebacterium efficiens*)
*Corynebacterium herculis*
*Brevibacterium divaricatum*
*Brevibacterium flavum*
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium ammoniagenes*
*Brevibacterium album*
*Brevibacterium cerinum*
*Microbacterium ammoniaphilum*,
*Microbacterium flavum* (*Corynebacterium flavescens*) etc.

Specific examples of the coryneform bacterium include, but are not limited to, strains such as *C. acetoacidophilum* ATCC 13870, *C. acetoglutamicum* ATCC 15806, *C. alkanolyticum* ATCC 21511, *C. callunae* ATCC 15991, *C. glutamicum* ATCC13020, ATCC 13032, ATCC 13060, ATCC 13869, *C. lilium* ATCC 15990, *C. melassecola* ATCC 17965, *C. thermoaminogenes* AJ12340 (FERM BP-1539), *C. herculis* ATCC 13868, *B. divaricatum* ATCC 14020, *B. flavum* ATCC 13826, ATCC 14067, AJ12418 (FERM BP-2205), *B. immariophilum* ATCC 14068, *B. lactofermentum* (*C. glutamicum*) ATCC 13869, *B. roseum* ATCC 13825 *B. saccharolyticum* ATCC 14066, *B. thiogenitalis* ATCC 19240, *B. ammoniagenes* ATCC 6871, ATCC 6872, *B. album* ATCC 15111, *B. cerinum* ATCC 15112, *Microbacterium ammoniaphilum* ATCC 15354, and so forth.

These strains are available from the American Type Culture Collection (ATCC, Address: P.O. Box 1549, Manassas, Va. 20108, United States of America). That is, each strain is given a unique registration number which is listed in the catalogue of the ATCC. Strains can be ordered using this registration number. The AJ 12340 strain was deposited at National Institute of Bioscience and Human Technology, Agency of Industrial Science and Technology, Ministry of International Trade and Industry (currently International Patent Organism Depositary, National Institute of Advanced Industrial Science and Technology at Tsukuba Central 6, 1-1, Higashi 1-chome, Tsukuba-shi, Ibaraki-ken 305-5466, Japan) on Oct. 27, 1989 under the provisions of the Budapest Treaty and given an accession number of FERM BP-1539. The AJ12418 strain was deposited at National Institute of Bioscience and Human Technology, Agency of Industrial Science and Technology, Ministry of International Trade and Industry on Jan. 5, 1989 under the provisions of the Budapest Treaty and given an accession number of FERM BP-2205.

The phrase "a bacterium belonging to the genus *Corynebacterium* or *Brevibacterium*" can mean that the bacterium is classified into the genus *Corynebacterium* or *Brevibacterium* according to the classification known to a person skilled in the art of microbiology. Examples of a bacterium belonging to the genus *Corynebacterium* or *Brevibacterium* include, but are not limited to, *Corynebacterium glutamicum* and *Brevibacterium flavum*.

The phrase "bacterium has been modified to attenuate expression of one or more gene(s) of the NCgl_2067-NCgl_2065 operon" can mean that the bacterium has been modified in such a way that the modified bacterium contains a reduced amount of one or more of the proteins, NCgl_2067, NCgl_2066 and NCgl_2065 as compared with an unmodified bacterium, or the modified bacterium is unable to synthesize the NCgl_2067, NCgl_2066 and/or NCgl_2065 protein(s). The phrase "bacterium has been modified to attenuate expression of one or more gene(s) of the NCgl_2067-NCgl_2065 operon" also can mean that the bacterium has been modified in such a way that the modified gene(s) encodes mutant NCgl_2067, NCgl_2066 and/or NCgl_2065 protein(s) with decreased activities. Since it is thought that genes NCgl_2067, NCgl_2066 and NCgl_2065 are organized as an operon, attenuation of expression of one of the genes can lead to polar effects on expression other genes of the NCgl_2067-NCgl_2065 operon.

The presence or absence of gene(s) of the NCgl_2067-NCgl_2065 operon in the chromosome of a bacterium can be detected by well-known methods, including PCR, Southern blotting, and the like. In addition, the level of gene expression can be determined by measuring the amount of mRNA transcribed from the gene using various well-known methods, including Northern blotting, quantitative RT-PCR, and the like. The amounts of the proteins encoded by the genes of the NCgl_2067-NCgl_2065 operon can be measured by well-known methods, including SDS-PAGE followed by an immunoblotting assay (Western blotting analysis), and the like.

The phrase "inactivation of one or more gene(s) of the NCgl_2067-NCgl_2065 operon" can mean that the modified gene(s) encodes a completely inactive protein(s). It is also possible that the modified DNA region is unable to naturally express the gene due to deletion of a part of or the entire gene, shifting of the reading frame of the gene, introduction of missense/nonsense mutation(s), or modification of an adjacent region of the gene, including sequences controlling gene expression, such as promoter(s), enhancer(s), attenuator(s), ribosome-binding site(s), etc.

The NCgl_2067 gene (synonyms—CG2358, Cg12147) codes for a hypothetical protein with unknown function. The NCgl_2067 gene of *C. glutamicum* (nucleotides complement to the nucleotides from 2270870 to 2270256 in the GenBank accession number NC_003450; gi: 58036263) is located between the NCgl_2066 and the ileS genes, on the chromosome of *C. glutamicum* ATCC 13032. The nucleotide sequence of the NCgl_2067 gene and the amino acid sequence of predicted NCgl_2067 protein encoded by the NCgl_2067 gene are shown in SEQ ID NO: 1 and SEQ ID NO: 2, respectively.

The NCgl_2066 gene (synonyms—CG2357, Cg12146) codes for a hypothetical putative transcriptional regulator. The NCgl_2066 gene of *C. glutamicum* (nucleotides complement to the nucleotides from 2,270,262 to 2,269,258 in the GenBank accession number NC_003450; gi: 58036263) is located between the NCgl_2067 and NCgl_2065 gene on the chromosome of *C. glutamicum* ATCC 13032, and both genes are oriented in the same direction as the NCgl_2066 gene, and these three genes are presumably organized as an operon. The nucleotide sequence of the NCgl_2066 gene and the amino acid sequence of predicted NCgl_2066 protein encoded by the NCgl_2066 gene are shown in SEQ ID NO: 3 and SEQ ID NO: 4, respectively.

The NCgl_2065 gene (synonyms-CG2356, Cg12145) is predicted to encode a DMT family permease. The NCgl_2065 gene of *C. glutamicum* (nucleotides complement to the nucleotides from 2,269,246 to 2,268,386 in the GenBank accession number NC_003450; gi: 58036263) is located between the NCgl_2066 and NCgl_2064 genes on the chromosome of *C. glutamicum* ATCC 13032. The nucleotide sequence of the NCgl_2066 gene and the amino acid sequence of predicted NCgl_2066 protein encoded by the NCgl_2066 gene are shown in SEQ ID NO: 5 and SEQ ID NO: 6, respectively.

Since there may be some differences in DNA sequences between the genera or strains of coryneform bacteria, genes of the NCgl_2067-NCgl_2065 operon to be inactivated on the chromosome are not limited to the genes shown in SEQ ID NO: 1, SEQ ID NO: 3 and SEQ ID NO: 5, but can include genes homologous to SEQ ID NO: 1, SEQ ID NO: 3, and SEQ ID NO: 5, which encode a variant proteins of the NCgl_2067, NCgl_2066 and NCgl_2065 proteins. The phrase "variant protein" can mean a protein which has changes in the sequence, whether they are deletions, insertions, additions, or substitutions of amino acids, but still maintains the activity of the product as the NCgl_2067, NCgl_2066 or NCgl_2065 protein. The number of changes in the variant protein depends on the position in the three dimensional structure of the protein or the type of amino acid residues. It can be 1 to 30, in another example 1 to 15, and in another example 1 to 5 in SEQ ID NO: 2, SEQ ID NO: 4, and SEQ ID NO:6. These changes in the variant can occur in regions of the protein which are not critical for the function of the protein. This is because some amino acids have high homology to one another so the three dimensional structure or activity is not affected by such a change. Therefore, the protein variant encoded by each gene of the NCgl_2067-NCgl_2065 operon can have a homology of not less than 80%, in another example not less than 90%, and in another example not less than 95%, in another example not less than 98%, in another example not less than 99%, with respect to the entire amino acid sequence shown in SEQ ID NO: 2, SEQ ID NO: 4, or SEQ ID NO:6, as long as the activity of the NCgl_2067, NCgl_2066 or NCgl_2065 protein prior to inactivation of each gene of the NCgl_2067-NCgl_2065 operon is maintained.

Homology between two amino acid sequences can be determined using well-known methods, for example, the computer program BLAST 2.0, which calculates three parameters: score, identity and similarity.

Moreover, each gene of the NCgl_2067-NCgl_2065 operon can be a variant which hybridizes under stringent conditions with the nucleotide sequence complementary to the sequence shown in SEQ ID NO: 1, SEQ ID NO: 3, or SEQ ID NO: 5, or a probe which can be prepared from the nucleotide sequence under stringent conditions, provided that it encodes a functional NCgl_2067, NCgl_2066, or NCgl_2065 protein prior to inactivation. "Stringent conditions" include those under which a specific hybrid, for example, a hybrid having homology of not less than 60%, in another example not less than 70%, in another example not less than 80%, in another example not less than 90%, and in another example not less than 95%, in another example not less than 98%, in another example not less than 99%, is formed and a non-specific hybrid, for example, a hybrid having homology lower than the above, is not formed. For example, stringent conditions can be exemplified by washing one time or more, or in another example, two or three times at a salt concentration of 1×SSC, 0.1% SDS, or in another example, 0.1×SSC, 0.1% SDS at 60° C. Duration of washing depends on the type of membrane used for blotting and, as a rule, can be what is recommended by the manufacturer. For example, the recommended duration of washing for the Hybond™ N+ nylon membrane (Amersham) under stringent conditions is 15 minutes. The washing step can be performed 2 to 3 times. The length of the probe can be suitably selected depending on the hybridization conditions, and is usually 100 bp to 1 kbp.

Expression of gene(s) of the NCgl_2067-NCgl_2065 operon can be attenuated by introducing a mutation into the gene(s) on the chromosome so that intracellular activity of the protein(s) encoded by the gene(s) are/is decreased as compared with an unmodified strain. Such a mutation on the gene can be replacement of one base or more to cause an amino acid substitution in the protein encoded by the gene (missense mutation), introduction of a stop codon (nonsense mutation), deletion of one or two bases to cause a frame shift, insertion of a drug-resistance gene, or deletion of a part of the gene or the entire gene (Qiu, Z. and Goodman, M. F., J. Biol. Chem. 1997, 272:8611-8617; Kwon, D. H. et al., J. Antimicrob. Chemother. 2000, 46:793-796). Expression of genes of the NCgl_2067-NCgl_2065 operon can also be attenuated by modifying an expression regulating sequence such as the promoter, the Shine-Dalgarno (SD) sequence, etc. (WO95/34672; Carrier, T. A. and Keasling, J. D., Biotechnol Prog 1999, 15:58-64).

For example, the following methods can be employed to introduce a mutation by gene recombination. A mutant gene encoding a mutant protein having a decreased activity is prepared, and the bacterium to be modified is transformed with a DNA fragment containing the mutant gene. Then the native gene on the chromosome is replaced with the mutant gene by homologous recombination, and the resulting strain is selected. Such gene replacement using homologous recombination can be conducted by a method employing a linear DNA, which is known as "Red-driven integration" (Datsenko, K. A. and Wanner, B. L., Proc. Natl. Acad. Sci. USA 2000, 97(12):6640-6645), or by methods employing a plasmid containing a temperature-sensitive replication origin (U.S. Pat. No. 6,303,383 or JP 05-007491A). Furthermore, the incorporation of a site-specific mutation by gene substitution using homologous recombination such as set forth above can also be conducted with a plasmid lacking the ability to replicate in the host.

Expression of the gene can also be attenuated by insertion of a transposon or an IS factor into the coding region of the gene (U.S. Pat. No. 5,175,107), or by conventional methods, such as a mutagenesis treatment using a UV irradiation or a mutagen such as nitrosoguanidine (N-methyl-N'-nitro-N-nitrosoguanidine).

Inactivation of the gene can also be performed by conventional methods, such as a mutagenesis treatment using UV irradiation or a mutagen such as nitrosoguanidine (N-methyl-N'-nitro-N-nitrosoguanidine), site-directed mutagenesis, gene disruption using homologous recombination, or/and insertion-deletion mutagenesis (Yu D. et al., Proc. Natl. Acad. Sci. USA 2000, 97(12):5978-83 and Datsenko, K. A. and Wanner, B. L., Proc. Natl. Acad. Sci. USA 2000, 97(12):6640-45), also called "Red-driven integration".

As L-glutamic acid is a precursor in biosynthesis of L-glutamine, L-proline, L-histidine L-arginine, L-ornithine, and L-citrulline, increasing production of L-glutamic acid results in increased production of a part or all of these amino acids.

Methods for preparation of plasmid DNA, digestion and ligation of DNA, transformation, selection of an oligonucleotide as a primer, and the like may be ordinary methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

L-Amino Acid-Producing Bacteria

As a bacterium in accordance with the presently disclosed subject matter which is modified to attenuate expression of one or more gene(s) of the NCgl_2067-NCgl_2065 operon, bacteria which are able to produce L-amino acids belonging to the glutamate family are described.

The bacterium in accordance with the presently disclosed subject matter can be obtained by attenuating expression of one or more genes of the NCgl_2067-NCgl_2065 operon in a bacterium which inherently has the ability to produce L-amino acids. Alternatively, the bacterium can be obtained by imparting the ability to produce L-amino acids to a bacterium already having the attenuated expression of one or more genes of the NCgl_2067-NCgl_2065 operon.

L-Glutamic Acid-Producing Bacteria

Examples of parent strains which can be used to derive L-glutamic acid-producing bacteria can include, but are not limited to, strains belonging to coryneform bacteria, such as strains *C. glutamicum* ATCC 13032, ATCC 31833, *C. acetoacidophilum* ATCC 13870, *C. herculis* ATCC 13868, *C. lilium* ATCC 15990, *B. divaricatum* ATCC 14020, *B. flavum* ATCC 14067, *B. imaliophilum* ATCC 14068, *B. lactofermentum* ATCC 13869, *B. thiogenitalis* ATCC 19240, and so forth.

Examples of parent strains which can be used to derive L-glutamic acid-producing bacteria also include strains in which expression of one or more genes encoding an L-glutamic acid enzyme are enhanced. Examples of such genes include genes encoding glutamate dehydrogenase, glutamine synthetase, glutamate synthetase, isocitrate dehydrogenase, aconitate hydratase, citrate synthase, phosphoenolpyruvate carboxylase, pyruvate carboxylase, pyruvate dehydrogenase, pyruvate kinase, phosphoenolpyruvate synthase, enolase, phosphoglyceromutase, phosphoglycerate kinase, glyceraldehyde-3-phosphate dehydrogenase, triose phosphate isomerase, fructose bisphosphate aldolase, phosphofructokinase, and glucose phosphate isomerase.

Methods of enhancing gene expression can include increasing the gene copy number by introducing a gene into a vector that is able to function in a coryneform bacterium. Gene expression can also be enhanced by introducing multiple copies of the gene into a bacterial chromosome by, for example, homologous recombination, Mu integration, or the like. The copy number of a gene can also be increased by introducing multiple copies of the gene into the chromosomal DNA of the bacterium. To introduce multiple copies of the gene into a bacterial chromosome, homologous recombination can be carried out using multiple copies of a sequence as targets in the chromosomal DNA. Gene expression can also be enhanced by placing the objective DNA under the control of a potent promoter.

Alternatively, the effect of a promoter can be enhanced by, for example, introducing a mutation into the promoter to increase the transcription level of a gene located downstream of the promoter. Furthermore, it is known that the substitution of several nucleotides in the spacer region between ribosome binding site (RBS) and the start codon, especially the sequences immediately upstream of the start codon, can profoundly affect the mRNA translatability. For example, a 20-fold range in the expression levels was found, depending on the nature of the three nucleotides preceding the start codon (Gold et al., Annu. Rev. Microbiol. 1981, 35:365-403; Hui et al., EMBO J. 1984, 3:623-629). Moreover, it is also possible to introduce a nucleotide substitution into a promoter region of a gene on the bacterial chromosome, which results in a stronger promoter function. The alteration of the expression control sequence can be performed, for example, in the same manner as the gene substitution using a temperature-sensitive plasmid, as disclosed in WO 00/18935 and JP 1-215280A.

Examples of microorganisms modified so that expression of the citrate synthetase gene, the phosphoenolpyruvate carboxylase gene, and/or the glutamate dehydrogenase gene is/are enhanced can include those microorganisms disclosed in the following: JP2001-333769A (EP1078989A), JP2000-106869A (EP955368A), JP2000-189169A (EP952221A), and JP2001-333769A (EP1078989A). Examples of a method of imparting L-glutamic acid-producing ability to coryneform bacterium can include increasing expression of the fasR gene and increasing of sensitivity to a surfactant (WO2007024010 A1). Examples of an L-glutamic acid-producing coryneform bacterium can include a strain which has been modified to enhance expression of the yggB gene (JP2007-097573 A).

Other examples of parent strains which can be used to derive L-glutamic acid-producing bacteria include strains in which expression of one or more genes encoding enzymes that catalyze synthesis of a compound other than L-glutamic acid, but which direct away from the L-glutamic acid biosynthesis pathway, are attenuated. Examples of such genes include genes encoding isocitrate lyase, β-ketoglutarate dehydrogenase, phosphotransacetylase, acetate kinase, acetohydroxy acid synthase, acetolactate synthase, formate acetyltransferase, lactate dehydrogenase, and glutamate decarboxylase. For attenuation of expression levels of such genes, the methods described above may be used.

Examples of L-glutamic acid-producing coryneform bacterium can include a strain in which the β-ketoglutarate dehydrogenase activity is decreased (JP7-834672A and JP06-237779), strain with inactive gluX gene (US 2010279363 A1), a strain with attenuated expression of sucC and/or sucD genes (EP1103611 A1), and so forth.

Specific examples of strains having an L-glutamic acid-producing ability can also include strains which are resistant to benzopirone or naphtoquinone (JP56-1889A), monofluoroacetic acid (JP 50-113209A), to adenine and thymine (JP57-065198), to β-ketomalonic acid (JP57-2689A), to guanidine (JP56-35981A), to daunomicin (JP58-158192A), and stains which are sensitive to penicillin (JP04-88994A).

Specific examples of L-glutamic acid-producing coryneform bacterium can also include the following strains: *B. flavum* AB949 (FERM BP-2632) (JP 50-113209A), AJ11355 (FERM P-5007) (JP56-1889A), AJ11217 (FERM P-4318) (JP57-2689A), AJ11564 (FERM P-5472) (JP56-140895A), AJ11439 (FERM P-5136) (JP56-35981A), *B. lactofermentum* AJ11426 (FERM P5123) (JP56-048890A), AJ11796 (FERM P6402) (JP58-158192A), *C. glutamicum* AJ11628 (FERM P-5736) (JP 57-065198A), AJ11440 (FERM P5137) (JP56-048890A), H7684 (FERM BP-3004; JP04-88994A), AJ11355 (FERM P-5020) (JP56-1889A), AJ11218 (FERM P-4319) (JP57-2689A).

L-Glutamine-Producing Bacteria

Examples of parent strains which can be used to derive L-glutamine-producing bacteria can include, but are not limited to, strains belonging to coryneform bacteria, such as strains *B. flavum* AJ11573 (FERM P-5492) (JP56-161495A) AJ11576 (FERM BP-10381) (JP56-161495A) AJ12212 (FERM P-8123) (JP61-202694A), AJ12418 (FERM BP-2205) (JP02-186994A), DH18 (FERM P-11116) (JP03-232497A), *C. glutamicum* AJ11574 (FERM P-5493) (JP56-151495A), *C. melassecola* DH344 (FERM P-11117) (JP3-232497A).

Examples of parent strains which can be used to derive L-glutamine-producing bacteria can also include strains in which expression of one or more genes encoding enzyme(s) of L-glutamine biosynthesis pathway are enhanced. Examples of such genes include genes encoding glutamine synthetase and glutamic acid dehydrogenase (U.S. Pat. No. 7,262,035 B2, EP1229121 B1), and the like.

Other examples of parent strains which can be used to derive L-glutamine-producing bacteria can also include strains in which expression of one or more genes encoding enzyme(s) that catalyze synthesis of compound other than L-glutamine, but which are directed away from the L-glutamine biosynthesis pathway, are attenuated. For attenuation of expression levels of such genes, the methods described above may be used. As a parent strain, an L-glutamine-producing strain with decreased glutaminase activity (EP1424397 B1), or a strain in which the gluABCD operon system for glutamine transport has been down-regulated or deleted (WO2008026698 A1) can be used, and the like.

Specific examples of strains having an L-glutamic acid-producing ability can also include strains which are resistant to an L-amino acid analog. Examples of parent strains can include strains resistant to 6-diazo-5-oxo-norleucine (JP-A-3-232497), to purine analogs and/or methionine sulfoxide (JP-A-61-202694), to β-ketomalonic acid (JP-A-56-151495), and so forth.

L-Histidine-Producing Bacteria

Examples of parent strains which can be used to derive L-histidine-producing bacteria include, but are not limited to, strains belonging to coryneform bacteria, such as strains *C. glutamicum* FERM BP-485 and FERM BP-486 (U.S. Pat. No. 4,495,283), *C. acetoacidophilum* AJ 1562 and *Microbacterium flavum* (*C. flavescens*) ATCC 10340 (JP 47002549 B), *C. glutamicum* AJ 12092 (FERM P-7273) and AJ 12426 (FERM BP-2213), *B. flavum* AJ 3420 (FERM P-2316) and *B. flavum* AJ 12425 (FERM BP-2212) (U.S. Pat. No. 5,294, 547), *C. glutamicum* (*B. flavum*) ATCC 21604 (VKPM B-1080) (U.S. Pat. No. 3,713,977), *C. glutamicum* ("*Micrococcus glutamicus*"); ATCC 13761; (NCIB 10334, VKPM B-4382) (U.S. Pat. No. 3,220,929), *C. glutamicum* ATCC 21339 (VKPM B-1003) (U.S. Pat. No. 3,676,301).

Specific examples of strains having an L-histidine-producing ability include strains belonging to coryneform bacteria, such as *B. flavum* FERM-P 2317, *B. lactofermentum* FERM-P 1565 (AJ 3386) *C. glutamicum* ATCC 14297 *B. lactofermentum* ATCC 21086 *C. acetoacidophilum* ATCC 21407, *B. flavum* ATCC 21406 (AJ 3225), and so forth.

Specific examples of strains having an L-histidine-producing ability include strains belonging to genus *Brevibacterium*, such as a strain *B. flavum* AJ11846 which is resistant to thiamin antagonists (2-thiazolalanine, triazolecarboxamid, and cobalamine) (JP 02018838 B), and *B. falvum* AJ 3579 strain which requires threonine, proline, shikimic acid, xanthine, or guanine and is resistant to 2-thiazolalanine. (JP 51024594).

L-Proline Producing Bacteria

Examples of parent strains which can be used to derive L-proline-producing bacteria can include, but are not limited to, strains belonging to coryneform bacteria, such as strains *B.*

*lactofermentum* AJ 11225 (FERM P-4370) (Japanese Patent Application Laid-Open No. 60-87788), *B. flavum* AJ 11512 (FERM P-5332), AJ 11513 (FERM P-5333), AJ 11514 (FERM P-5334), *C. glutamicum* AJ 11522 (FERM P-5342), AJ 11523 (FERM P-5343) (see Japanese Patent Publication No. 62-36679), and so forth.

Examples of parent strains which can be used to derive L-proline producing bacteria also include strains in which expression of one or more genes encoding an L-proline biosynthetic enzyme are enhanced. Examples of an L-proline-biosynthetic enzyme include glutamate kinase, γ-glutamyl phosphate reductase, and pyrroline-5-carboxylate reductase (Ankri S et al., J. Bacteriol. 1996, 178(15):4412-4419). Also, L-proline producing bacteria can be used which have decreased activity of an enzyme that catalyzes a reaction which is directed away from the L-proline biosynthetic pathway and results in the production of other compounds. For example, L-proline-producing ability may be imparted by decreasing ornithine-aminotransferase activity (J. Bacteriol. 1996 August; 178(15):4412-9).

L-Arginine-Producing Bacteria

Examples of parent strains which can be used to derive L-arginine-producing bacteria can include, but are not limited to, strains belonging to coryneform bacteria, such as strains *C. glutamicum* AJ12092 and *B. flavum* AJ11169 (EP 378223 B1, JP 2817155 B2, U.S. Pat. No. 5,284,757 A), *B. flavum* AJ 12144 (FERM P-7642) and *C. glutamicum* AJ 12145 (FERM P-7643) (Japanese Patent Publication No. 5-27388), *B. flavum* ATCC 21493 and *C. glutamicum* ATCC 21659; (Japanese Patent Application Laid-Open No. 5-3793), *B. flavum* FERM-P 4948, *C. glutamicum* FERM-P 7274 (AJ 12093), *B. flavum* NRRL 12235 (AJ 11337) *C. acetoglutamicum* NRRL 12239 (AJ 11342).

It is known that an L-arginine-producing ability can also be efficiently enhanced by using a mutant N-acetylglutamate kinase which is resistant to feedback inhibition by L-arginine (WO 2006035831 A1).

Specific examples of strains having an L-arginine-producing ability include strains belonging to the genus *Brevibacterium* or *Corynebacterium*, and which are resistant to arginine hydroxamate, arginine antagonists, argininol, sulfamides, cysteine or its analogs (EP 336387 B1, JP 2578468 B2, U.S. Pat. No. 5,034,319 A), aliphatic guanidine or aliphatic chain derivative guanidine (JP 2817155 B2, EP 0378223 B1), and so forth. The productivity of L-arginine strains of coryneform bacterium can be also improved by imparting resistance to sulfa drugs or argininol, or resistance to chemicals such as 8-azaguanine, alpha-amino-beta-hydroxyvaleric acid, etc.

Examples of parent strains which can be used to derive L-arginine producing bacteria also include strains auxotrophic for amino acids such as L-histidine, L-proline, L-threonine, L-tryptophan, L-lysine, etc. Examples of parent strains which can be used to derive L-arginine producing bacteria also include strains that are known as citrulline or arginine auxotrophs (Japanese Patent Publication No. 43-8712), variants of arginine auxotroph (Japanese Patent Application Laid-Open No. 53-24096), variants belonging to the genus *Corynebacterium* having a resistance to 2-thiazole-alanine, sulfaguanidine or 2-fluoropyruvic acid (Japanese Patent Application Laid-Open No. 61-119194) and so forth.

Examples of parent strains which can be used to derive L-arginine producing bacteria also include strains in which expression of one or more genes encoding an L-arginine biosynthetic enzyme are enhanced. Examples of such genes include genes encoding N-acetylglutamyl phosphate reductase (argC), ornithine acetyl transferase (argJ), N-acetyl-glutamate kinase (argB), acetylornithine transaminase (argD), ornithine carbamoyl transferase (argF), argininosuccinic acid synthetase (argG), argininosuccinic acid lyase (argH), and carbamoyl phosphate synthetase (carAB).

L-arginine producing bacterium can be improved by inactivation of the arginine repressor encoded by argR gene. Methods for inactivation of argR gene are described above.

L-Ornithine Producing Bacteria

Examples of parent strains which can be used to derive L-ornithine-producing bacteria include, but are not limited to, strains belonging to coryneform bacteria, such as strains *B. lactofermentum* FERM BP-2344, FERM-P 5936 (AJ 11678) and *C. glutamicum* FERM BP-2345 (JP 2817185 (B2), EP 393708 B1), *C. glutamicum* FERM-P 5644 (AJ 11589), ATCC 13232, and the like.

As L-ornithine is an intermediate of L-arginine biosynthetic pathway, examples of parent strains, which can be used to derive L-ornithine-producing bacteria include strains in which expression of one or more genes encoding an L-arginine biosynthetic enzyme is enhanced. L-ornithine producing bacterium can be easily obtained from any arginine producing bacterium, by inactivation of ornithine carbamoyltransferase encoded by both argF and argI genes. Methods for inactivation of ornithine carbamoyltransferase are described above.

L-Citrulline Producing Bacteria

Examples of parent strains which can be used to derive L-citrulline-producing bacteria include, but are not limited to, strains belonging to coryneform bacteria, strains *C. glutamicum* FERM-P 5643 (AJ 11588), *B. flavum* FERM-P 1645 (AJ 3408), and so forth.

As L-citrulline is an intermediate in the L-arginine biosynthetic pathway, examples of parent strains, which can be used to derive L-citrulline producing bacterium can be easily obtained from any L-arginine producing bacterium, for example, by inactivation of argininosuccinate synthase encoded by argG gene.

2. Method of the Present Invention

In a method for producing an L-amino acid of the presently disclosed subject matter, the bacterium as described herein is cultured in a culture medium to produce and excrete the L-amino acid into the medium, and the L-amino acid is collected from the medium.

The cultivation of the bacterium, collection, and purification of an L-amino acid from the medium and the like may be performed in a manner similar to conventional fermentation methods wherein an amino acid is produced using a bacterium.

The medium used for culture may be either a synthetic or natural medium, so long as the medium includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation can be performed under aerobic conditions, such as a shaking culture, and a stirring culture with aeration, at a temperature of 20 to 40° C., or 30 to 38° C. The pH of the culture is usually between 5 and 9, or between 6.5 and 7.2.

The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the L-amino acid can be collected and purified by ion-exchange, concentration, and/or crystallization methods.

EXAMPLES

The present invention will be more concretely explained below with reference to the following non-limiting Examples.

Example 1

Figure 1:
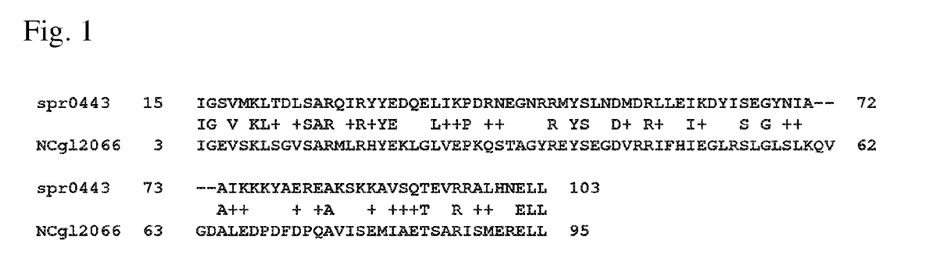
FIG. 1 shows alignment of the GlnR (denoted as spr0433) protein from *Streptococcus pneumoniae* R6 and putative NCgl_2066 protein from *Corynebacterium glutamicum* ATCC13032.
Figure 2:
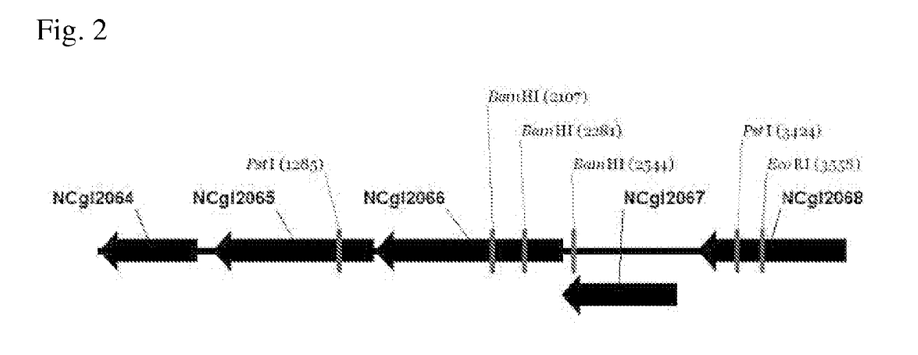
FIG. 2 shows structure of the NCgl_2067-NCgl_2065 operon from *Corynebacterium glutamicum* ATCC13032
Figure 3:
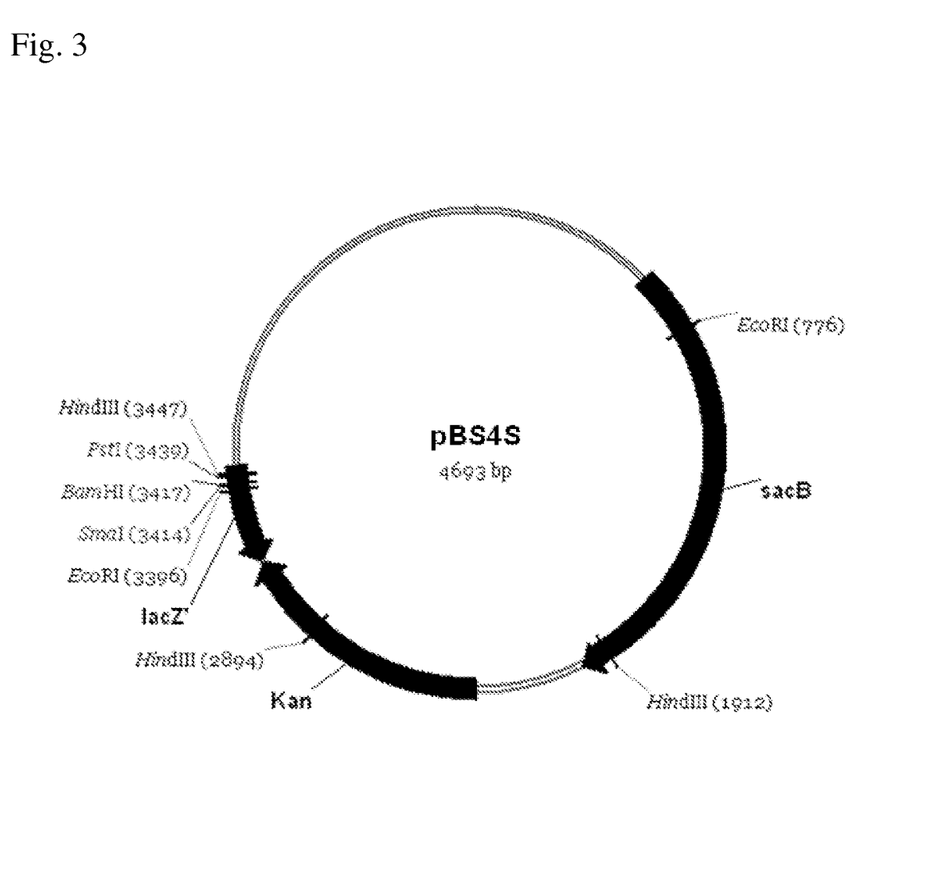
FIG. 3 shows structure of the pBS4S plasmid.

Construction of a Strain with Attenuated Expression of NCgl_2067 Gene 1-1. Deletion of the NCgl_2067 Gene A strain in which the NCgl_2067 gene is deleted was constructed by using the non-replicative plasmid pSB4S (see FIG. 3; the construction of the plasmid is described in U.S. Pat. No. 7,794,989). The in-frame deletion of the NCgl_2067 gene was constructed. For this purpose, overlap extension PCR was conducted. First, a DNA fragment was obtained by PCR with primers NC2067F (SEQ ID NO: 7) and NC2067R1 (SEQ ID NO: 8) and chromosomal DNA of B. flavum B-6642 (described in patent of Russian Federation RU 2084520° C.2) as the template. The strain B. flavum B-6642 was deposited as an international deposit at the Russian National Collection of Industrial Microorganisms (VKPM) (1 Dorozhny proezd., 1 Moscow 117545, Russia) on Jun. 28, 1993 under the accession number of VKPM B-6642 and then converted to a deposit under the Budapest Treaty on Mar. 5, 2012.

Second, a DNA fragment was obtained using PCR with oligonucleotides NC2067F1 (SEQ ID NO: 9) and NC2067R (SEQ ID NO: 10) and chromosomal DNA of B. flavum B-6642 as the template. After that, the two DNA fragments described above were used as the template in the first round of PCR with primers NC2067-SmF (SEQ ID NO: 11) and NC2067-SmR (SEQ ID NO: 12). Conditions for all PCRs were as follows: denaturation step for 30 sec at 94° C.; profile for 25 cycles: 30 sec at 94° C., 30 sec at 58° C., 60 sec at 72° C.; final step: 2 min at 72° C.

After that, the obtained PCR product was purified and treated with endonuclease SmaI and then ligated into a SmaI-cleaved plasmid pBS4S to obtain pBS4SΔ2067.

Electrocompetent cells were prepared as follows: B. flavum B-6642 was grown overnight at 30° C. in CM2GxYE medium (peptone—10 g/l, yeast extract—20 g/l, NaCl—5 g/l, glucose—5 g/l, pH is adjusted to 7.0), and then the culture was diluted about 20 times with fresh CM2GxYE medium. The cells were grown with aeration at 30° C. to an OD600 of ≈0.6 and ampicillin was added (10 μg/ml) and cultivated for 1 hour. The obtained cells were washed three times with ice-cold deionized H2O. Electroporation was performed using 50 μl of cells and ≈5 μg of the plasmid pBS4SΔ2067 with the following parameters: 2.0 kV, 0.1 cm electrode gap. Cells after electroporation were incubated with 1 ml CM2GxYE medium at 30° C. for 2 hours with shaking and then were plated onto 2LA-agar (peptone—10 g/l, yeast extract—10 g/l, NaCl—5 g/l, agar—20 g/l, pH is adjusted to 7.0) containing kanamycin (25 μg/ml) and grown at 30° C. to select KmR recombinants for 48 h. The obtained integrants were also unable to grow on 2LA medium containing 10% sucrose.

1-2. Verification of the NCgl_2067 Gene Deletion by PCR

The mutants in which the NCgl_2067 gene was deleted were verified by PCR. Locus-specific primers P1 (SEQ ID NO: 13) and P2 (SEQ ID NO: 14) were used in PCR for the verification. The PCR product obtained in the reaction with the cells of the parental strain B. flavum B-6642 as the template, was ~1.35 kbp in length. The PCR product obtained in the reaction with the cells of mutant strain as the template was ~0.78 kbp in length. Deletion of NCgl_2067 gene was also confirmed by the sequencing of the corresponding chromosomal DNA fragment. The mutant strain was given the name B. flavum B-6642ΔNCgl_2067.

Example 2

Construction of a Strain with Attenuated Expression of NCgl_2066 Gene 2-1. Deletion of the NCgl_2066 Gene A strain in which the NCgl_2066 gene was deleted was constructed in the same manner as described in Example 1. The in-frame deletion of the NCgl_2066 gene was constructed. For this purpose, overlap extension PCR was conducted. First, a DNA fragment was obtained in PCR with primers NC2066F (SEQ ID NO: 15) and NC2066R1 (SEQ ID NO: 16) and chromosomal DNA of B. flavum B-6642 as the template. Second, a DNA fragment was obtained in PCR with oligonucleotides NC2066F1 (SEQ ID NO: 17) and NC2066R (SEQ ID NO: 18) and chromosomal DNA of B. flavum B-6642 as the template. After that, the two DNA fragments described above were used as the template in the first round of PCR with primers NC2066-SmF (SEQ ID NO: 19) and NC2066-SmR (SEQ ID NO: 20). After that, the obtained PCR product was purified and treated with endonuclease SmaI, and then ligated into SmaI-cleaved plasmid pBS4S to obtain pBS4SΔ2066.

Electrocompetent cells were prepared as follows: B. flavum B-6642 was grown overnight at 30° C. in CM2GxYE medium (peptone—10 g/l, yeast extract—20 g/l, NaCl—5 g/l, glucose—5 g/l, pH is adjusted to 7.0), and then the culture was diluted about 20 times with fresh CM2GxYE medium. The cells were grown with aeration at 30° C. to an OD600 of ≈0.6 and ampicillin was added (10 μg/ml) and cultivated for 1 hour. The obtained cells were washed three times with ice-cold deionized H2O. Electroporation was performed using 50 μl of cells and ≈5 μg of the plasmid pBS4SΔ2066 with the following parameters: 2.0 kV, 0.1 cm electrode gap. Cells after electroporation were incubated with 1 ml CM2GxYE medium at 30° C. for 2 hours with shaking and then were plated onto 2LA-agar (peptone—10 g/l, yeast extract—10 g/l, NaCl—5 g/l, agar—20 g/l, pH is adjusted to 7.0) containing kanamycin (25 μg/ml) and grown at 30° C. to select KmR recombinants for 48 h. The obtained integrants were also unable to grow on 2LA medium containing 10% sucrose.

2-2. Verification of the NCgl_2066 Gene Deletion by PCR

The mutants in which the NCgl_2066 gene was deleted were verified by PCR. Locus-specific primers NC2066F (SEQ ID NO: 15) and NC2066R (SEQ ID NO: 18) were used in PCR for the verification. The PCR product obtained in the reaction with the cells of parental strain B. flavum B-6642 as the template, was ~2.12 kbp in length. The PCR product obtained in the reaction with the cells of mutant strain as the template was ~1.15 kbp in length. Deletion of the NCgl_2066 gene was also confirmed by the sequencing of the corresponding chromosomal DNA fragment. The mutant strain was given the name B. flavum B-6642ΔNCgl_2066.

Example 3

Production of L-Glutamic Acid and L-Glutamine by B. Flavum Strain B-6642ΔNCgl_2067

B. flavum strains, B-6642ΔNCgl_2067, and B-6642, were separately grown for 18-24 hours at 30° C. on 2LA-agar plates. Then, one loop of the cells was transferred into test tubes containing 2 ml of fermentation medium. The fermentation medium contains $(NH_4)_2SO_4$ (70 g/l), $KH_2PO_4$ (2.5 g/l), thiamine (350 mg/l), biotin (100 mg/l), $MgSO_4$ $7H_2O$ (0.4 g/l), Mameno (soybean protein hydrolysate, 5.7 mg/l), sucrose (120 g/l), and CaCO3 (50 g/l). The pH is adjusted to 7.

Cultivation was carried out at 30° C. for 48 hours with shaking. After the cultivation, the amount of L-glutamic acid (Glu) and L-glutamine (Gln) which are produced was determined by TLC (thin-layer chromatography) using the following mobile phase: butanol:acetic acid:water=4:1:1 (v/v). A solution of ninhydrin (1%) in acetone was used as a visualizing reagent. The spots containing L-glutamic acid and L-glutamine were cut out, and L-glutamic acid and L-glutamine were eluted with 0.5% water solution of $CdCl_2$. The amounts were estimated spectrophotometrically at 540 nm. The results of two independent test tube fermentations are shown in Table 1. As follows from Table 1, strain B-6642ΔNCgl_2067 with attenuated expression of NCgl_2067 gene produced higher amounts of L-glutamic acid and L-glutamine, as compared with the parent strain B-6642.

TABLE 1

| Strain | Gln, g/l | Glu, g/l |
| --- | --- | --- |
| B-6642 | 3.9 ± 0.1 | 4.2 ± 0.2 |
| B-6642ΔNCgl_2067 | 4.4 ± 0.3 | 4.6 ± 0.1 |

Example 4

Production of L-Glutamic Acid and L-Glutamine by B. Flavum Strain B-6642Δ NCgl_2066

B. flavum strains, B-6642ΔNCgl_2066 and B-6642, were separately grown for 18-24 hours at 30° C. on 2LA-agar plates. Then, one loop of the cells was transferred into test tubes containing 2 ml of fermentation medium. The fermentation medium contains $(NH_4)_2SO_4$ (70 g/l), $KH_2PO_4$ (2.5 g/l), thiamine (350 mg/l), biotin (100 mg/l), $MgSO_4$ $7H_2O$ (0.4 g/l), Mameno (5.7 mg/l), sucrose (120 g/l), and $CaCO_3$ (50 g/l). The pH is adjusted to 7.

Cultivation was carried out at 30° C. for 48 hours with shaking. After the cultivation, the amount of L-glutamic acid and L-glutamine which is produced was determined by TLC (thin-layer chromatography) using the following mobile phase: butanol:acetic acid:water=4:1:1 (v/v). A solution of ninhydrin (1%) in acetone was used as a visualizing reagent. The spots containing L-glutamic acid and L-glutamine were cut out, L-glutamic acid and L-glutamine were eluted with 0.5% water solution of $CdCl_2$, and the amounts were estimated spectrophotometrically at 540 nm.

The results of two independent test tube fermentations are shown in Table 2. As follows from Table 2, strain B-6642ΔNCgl_2066 with attenuated expression of NCgl_2066 gene produced higher amounts of L-glutamic acid and L-glutamine, as compared with the parent strain B-6642.

TABLE 2

| Strain | Gln, g/l | Glu, g/l |
| --- | --- | --- |
| B-6642 | 4.8 ± 0.1 | 3.9 ± 0.1 |
| B-6642ΔNCgl_2066 | 5.8 ± 0.3 | 4.3 ± 0.1 |

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, an L-amino acid belonging to the glutamate family is efficiently produced by a coryneform bacterium.

The invention claimed is:

1. A method for producing an L-amino acid belonging to the glutamate family comprising:
cultivating a coryneform bacterium which is able to produce an L-amino acid belonging to the glutamate family, wherein said bacterium has been modified to attenuate the expression of one or more gene(s) of the NCgl 2067-NCgl 2065 operon in a medium, and
collecting said L-amino acid from the medium.

2. The method according to claim 1, wherein said L-amino acid is selected from the group consisting of L-glutamic acid, L-glutamine, L-proline, L-histidine, L-arginine, L-ornithine, L-citrulline, and combinations thereof.

3. The method according to claim 2, wherein said L-amino acid is selected from the group consisting of L-glutamic acid, L-glutamine, and combinations thereof.

4. The method according to claim 1, wherein said bacterium has been modified to attenuate the expression of the NCgl_2067 gene.

5. The method according to claim 4, wherein said expression of the NCgl_2067 gene is attenuated by inactivation of the NCgl_2067 gene.

6. The method according to claim 1, wherein said bacterium has been modified to attenuate the expression of the NCgl_2066 gene.

7. The method according to claim 1, wherein said expression of the NCgl_2066 gene is attenuated by inactivation of the NCgl_2066 gene.

8. The method according to claim 1, wherein said bacterium belongs to the genus *Corynebacterium* or *Brevibacterium*.

9. The method according to claim 8, wherein said bacterium is *Brevibacterium flavum*.

10. The method according to claim 4, wherein said L-amino acid is selected from the group consisting of L-glutamic acid, L-glutamine, L-proline, L-histidine, L-arginine, L-ornithine, L-citrulline, and combinations thereof.

11. The method according to claim 10, wherein said L-amino acid is selected from the group consisting of L-glutamic acid, L-glutamine, and combinations thereof.

12. The method according to claim 5, wherein said L-amino acid is selected from the group consisting of L-glutamic acid, L-glutamine, L-proline, L-histidine, L-arginine, L-ornithine, L-citrulline, and combinations thereof.

13. The method according to claim 12, wherein said L-amino acid is selected from the group consisting of L-glutamic acid, L-glutamine, and combinations thereof.

14. The method according to claim 6, wherein said L-amino acid is selected from the group consisting of L-glutamic acid, L-glutamine, L-proline, L-histidine, L-arginine, L-ornithine, L-citrulline, and combinations thereof.

15. The method according to claim 14, wherein said L-amino acid is selected from the group consisting of L-glutamic acid, L-glutamine, and combinations thereof.

16. The method according to claim 7, wherein said L-amino acid is selected from the group consisting of L-glutamic acid, L-glutamine, L-proline, L-histidine, L-arginine, L-ornithine, L-citrulline, and combinations thereof.

17. The method according to claim 16, wherein said L-amino acid is selected from the group consisting of L-glutamic acid, L-glutamine, and combinations thereof.

18. The method according to claim 8, wherein said L-amino acid is selected from the group consisting of L-glutamic acid, L-glutamine, L-proline, L-histidine, L-arginine, L-ornithine, L-citrulline, and combinations thereof.

19. The method according to claim 18, wherein said L-amino acid is selected from the group consisting of L-glutamic acid, L-glutamine, and combinations thereof.

20. The method according to claim 9, wherein said L-amino acid is selected from the group consisting of L-glutamic acid, L-glutamine, L-proline, L-histidine, L-arginine, L-ornithine, L-citrulline, and combinations thereof.

21. The method according to claim 20, wherein said L-amino acid is selected from the group consisting of L-glutamic acid, L-glutamine, and combinations thereof.

* * * * *

UNITED STATES PATENT AND TRADEMARK OFFICE
CERTIFICATE OF CORRECTION

PATENT NO.       : 9,029,104 B2
APPLICATION NO.  : 14/045205
DATED            : May 12, 2015
INVENTOR(S)      : Samsonova et al.

It is certified that error appears in the above-identified patent and that said Letters Patent is hereby corrected as shown below:

Claims

In Column 31, lines 46-48, please amend Claim 7 as follows:

7. The method according to claim 6, wherein said expression of the *NCgl_2066* gene is attenuated by inactivation of the *NCgl_2066* gene.

Signed and Sealed this
Eighth Day of March, 2016

Michelle K. Lee
*Director of the United States Patent and Trademark Office*

SEQUENCE LISTING

```
<160> NUMBER OF SEQ ID NOS: 20

<210> SEQ ID NO 1
<211> LENGTH: 615
<212> TYPE: DNA
<213> ORGANISM: Corynebacterium glutamicum
<220> FEATURE:
<221> NAME/KEY: CDS
<222> LOCATION: (1)..(615)

<400> SEQUENCE: 1 atg gac aac ttc gaa cat tca aat gca tct atc cgt tta caa gca gcg      48
Met Asp Asn Phe Glu His Ser Asn Ala Ser Ile Arg Leu Gln Ala Ala
1               5                   10                  15 ttg gcc gca gga act gct gag gac acc act gcg atc gat att ctt ttg      96
Leu Ala Ala Gly Thr Ala Glu Asp Thr Thr Ala Ile Asp Ile Leu Leu
            20                  25                  30
```

| | | | | | | | | | | | | | | | |
|---|---|---|---|---|---|---|---|---|---|---|---|---|---|---|---|
| tac | cgc | agt | ggg | gta | gaa | gaa | gac | ttc | ttt | gtg | cgc | gac | atg | atc | acg | 144
| Tyr | Arg | Ser | Gly | Val | Glu | Glu | Asp | Phe | Phe | Val | Arg | Asp | Met | Ile | Thr |
| | | 35 | | | | 40 | | | | | 45 | | | | |

| tgg | gcg | ctc | acc | cgc | atg | cca | gtt | gat | gac | gtg | ttt | acc | tca | ctg | gtc | 192
| Trp | Ala | Leu | Thr | Arg | Met | Pro | Val | Asp | Asp | Val | Phe | Thr | Ser | Leu | Val |
| 50 | | | | | 55 | | | | | 60 | | | | | |

| gct | gat | ttg | gat | tct | gag | gta | cct | gat | cga | cca | ttc | ggt | gca | agt | caa | 240
| Ala | Asp | Leu | Asp | Ser | Glu | Val | Pro | Asp | Arg | Pro | Phe | Gly | Ala | Ser | Gln |
| 65 | | | | 70 | | | | | 75 | | | | | 80 | |

| gca | ctc | cac | aca | ctc | tcc | aag | tta | agg | gtc | gcg | cag | tcg | tgg | cag | gaa | 288
| Ala | Leu | His | Thr | Leu | Ser | Lys | Leu | Arg | Val | Ala | Gln | Ser | Trp | Gln | Glu |
| | | | | 85 | | | | | 90 | | | | | 95 | |

| ttg | caa | gca | cgg | cct | tgg | ctt | ttg | cac | cgg | gag | gac | acc | gcc | caa | act | 336
| Leu | Gln | Ala | Arg | Pro | Trp | Leu | Leu | His | Arg | Glu | Asp | Thr | Ala | Gln | Thr |
| | | | 100 | | | | | 105 | | | | | 110 | | |

| gcg | tgg | cga | acc | ttt | gtg | gga | ctg | gtc | cca | gat | gat | cag | acc | gca | tgg | 384
| Ala | Trp | Arg | Thr | Phe | Val | Gly | Leu | Val | Pro | Asp | Asp | Gln | Thr | Ala | Trp |
| | | | 115 | | | | | 120 | | | | | 125 | | |

| ttg | gcg | cac | caa | ttg | ctc | caa | gaa | ttg | gat | aaa | gga | acg | cct | gaa | att | 432
| Leu | Ala | His | Gln | Leu | Leu | Gln | Glu | Leu | Asp | Lys | Gly | Thr | Pro | Glu | Ile |
| | 130 | | | | | 135 | | | | | 140 | | | | |

| cag | cgg | agt | tta | agt | cgg | gcg | atg | gcg | gaa | ttg | gag | ggg | agg | gag | gcg | 480
| Gln | Arg | Ser | Leu | Ser | Arg | Ala | Met | Ala | Glu | Leu | Glu | Gly | Arg | Glu | Ala |
| 145 | | | | | 150 | | | | | 155 | | | | | 160 |

| tcg | ata | agc | gtg | ctt | cta | ggc | gct | tta | acg | agc | gcg | cac | gcg | gtg | gcc | 528
| Ser | Ile | Ser | Val | Leu | Leu | Gly | Ala | Leu | Thr | Ser | Ala | His | Ala | Val | Ala |
| | | | | 165 | | | | | 170 | | | | | 175 | |

| acc | gcc | aag | ctc | att | gcg | gat | ccg | gac | tcc | gat | ttc | atg | gct | gat | ctg | 576
| Thr | Ala | Lys | Leu | Ile | Ala | Asp | Pro | Asp | Ser | Asp | Phe | Met | Ala | Asp | Leu |
| | | | 180 | | | | | 185 | | | | | 190 | | |

| gag | gaa | gcg | cgg | cgc | gtg | gat | aat | atg | ggt | gca | tgc | tga | | | | 615
| Glu | Glu | Ala | Arg | Arg | Val | Asp | Asn | Met | Gly | Ala | Cys | | | | |
| | | 195 | | | | | 200 | | | | | | | | |

```
<210> SEQ ID NO 2
<211> LENGTH: 204
<212> TYPE: PRT
<213> ORGANISM: Corynebacterium glutamicum

<400> SEQUENCE: 2
```

| Met | Asp | Asn | Phe | Glu | His | Ser | Asn | Ala | Ser | Ile | Arg | Leu | Gln | Ala | Ala |
|---|---|---|---|---|---|---|---|---|---|---|---|---|---|---|---|
| 1 | | | | 5 | | | | | 10 | | | | | 15 | |

| Leu | Ala | Ala | Gly | Thr | Ala | Glu | Asp | Thr | Thr | Ala | Ile | Asp | Ile | Leu | Leu |
|---|---|---|---|---|---|---|---|---|---|---|---|---|---|---|---|
| | | | 20 | | | | | 25 | | | | | 30 | | |

| Tyr | Arg | Ser | Gly | Val | Glu | Glu | Asp | Phe | Phe | Val | Arg | Asp | Met | Ile | Thr |
|---|---|---|---|---|---|---|---|---|---|---|---|---|---|---|---|
| | | 35 | | | | 40 | | | | | 45 | | | | |

| Trp | Ala | Leu | Thr | Arg | Met | Pro | Val | Asp | Asp | Val | Phe | Thr | Ser | Leu | Val |
|---|---|---|---|---|---|---|---|---|---|---|---|---|---|---|---|
| 50 | | | | | 55 | | | | | 60 | | | | | |

| Ala | Asp | Leu | Asp | Ser | Glu | Val | Pro | Asp | Arg | Pro | Phe | Gly | Ala | Ser | Gln |
|---|---|---|---|---|---|---|---|---|---|---|---|---|---|---|---|
| 65 | | | | 70 | | | | | 75 | | | | | 80 | |

| Ala | Leu | His | Thr | Leu | Ser | Lys | Leu | Arg | Val | Ala | Gln | Ser | Trp | Gln | Glu |
|---|---|---|---|---|---|---|---|---|---|---|---|---|---|---|---|
| | | | | 85 | | | | | 90 | | | | | 95 | |

| Leu | Gln | Ala | Arg | Pro | Trp | Leu | Leu | His | Arg | Glu | Asp | Thr | Ala | Gln | Thr |
|---|---|---|---|---|---|---|---|---|---|---|---|---|---|---|---|
| | | | 100 | | | | | 105 | | | | | 110 | | |

| Ala | Trp | Arg | Thr | Phe | Val | Gly | Leu | Val | Pro | Asp | Asp | Gln | Thr | Ala | Trp |
|---|---|---|---|---|---|---|---|---|---|---|---|---|---|---|---|
| | | | 115 | | | | | 120 | | | | | 125 | | |

| Leu | Ala | His | Gln | Leu | Leu | Gln | Glu | Leu | Asp | Lys | Gly | Thr | Pro | Glu | Ile |
|---|---|---|---|---|---|---|---|---|---|---|---|---|---|---|---|
| | 130 | | | | | 135 | | | | | 140 | | | | |

```
Gln Arg Ser Leu Ser Arg Ala Met Ala Glu Leu Glu Gly Arg Glu Ala
145                 150                 155                 160

Ser Ile Ser Val Leu Leu Gly Ala Leu Thr Ser Ala His Ala Val Ala
            165                 170                 175

Thr Ala Lys Leu Ile Ala Asp Pro Asp Ser Asp Phe Met Ala Asp Leu
        180                 185                 190

Glu Glu Ala Arg Arg Val Asp Asn Met Gly Ala Cys
    195                 200

<210> SEQ ID NO 3
<211> LENGTH: 1005
<212> TYPE: DNA
<213> ORGANISM: Corynebacterium glutamicum
<220> FEATURE:
<221> NAME/KEY: CDS
<222> LOCATION: (1)..(1005)

<400> SEQUENCE: 3 atg ctg atc ggt gag gtg tcc aag ctc agt ggg gtg agt gcg cgc atg    48
Met Leu Ile Gly Glu Val Ser Lys Leu Ser Gly Val Ser Ala Arg Met
1               5                   10                  15 ttg cgg cac tac gaa aag ctg ggt ttg gtc gag ccg aag cag tcg acg    96
Leu Arg His Tyr Glu Lys Leu Gly Leu Val Glu Pro Lys Gln Ser Thr
            20                  25                  30 gcg ggg tat cgg gaa tac tca gaa ggc gat gtg cgc agg att ttc cat   144
Ala Gly Tyr Arg Glu Tyr Ser Glu Gly Asp Val Arg Arg Ile Phe His
        35                  40                  45 atc gaa ggt ttg cgc agc ttg ggt ctt agt ttg aag cag gtt gga gac   192
Ile Glu Gly Leu Arg Ser Leu Gly Leu Ser Leu Lys Gln Val Gly Asp
    50                  55                  60 gcg ctt gag gat cca gac ttt gat cct cag gca gtc att tcc gag atg   240
Ala Leu Glu Asp Pro Asp Phe Asp Pro Gln Ala Val Ile Ser Glu Met
65                  70                  75                  80 att gct gag act tct gcg cgg att tct atg gaa cgg gag ttg ctt gcc   288
Ile Ala Glu Thr Ser Ala Arg Ile Ser Met Glu Arg Glu Leu Leu Ala
                85                  90                  95 agg ctg aaa gcg gtg cgt cat gcg cag gcc tcg gat tgg gaa tcg gcg   336
Arg Leu Lys Ala Val Arg His Ala Gln Ala Ser Asp Trp Glu Ser Ala
            100                 105                 110 ttg gat gcg gtg cag att tta cgt cgc ctg cga tcg ggg gat ccg gcg   384
Leu Asp Ala Val Gln Ile Leu Arg Arg Leu Arg Ser Gly Asp Pro Ala
        115                 120                 125 caa cgt caa gcc gtg gcc tat gac tct gtc tct ggt aaa gaa gca gtt   432
Gln Arg Gln Ala Val Ala Tyr Asp Ser Val Ser Gly Lys Glu Ala Val
    130                 135                 140 gcg cta gaa acc ttg gtg gaa tcg gcg ctc ggt gag tcg cat ttg aac   480
Ala Leu Glu Thr Leu Val Glu Ser Ala Leu Gly Glu Ser His Leu Asn
145                 150                 155                 160 gcg gag ggg gcg ctg tcg tgg gcg gtt gtg cag cgt ggt gag gaa gct   528
Ala Glu Gly Ala Leu Ser Trp Ala Val Val Gln Arg Gly Glu Glu Ala
                165                 170                 175 gtt gca ttg gcg gca cga ggt ttg cgc tca agg gat gcg gcg gtg cgg   576
Val Ala Leu Ala Ala Arg Gly Leu Arg Ser Arg Asp Ala Ala Val Arg
            180                 185                 190 ctg cgg gct gta agg att gtg gcg agc gcg ccg agt gct gtt gcg gat   624
Leu Arg Ala Val Arg Ile Val Ala Ser Ala Pro Ser Ala Val Ala Asp
        195                 200                 205 cga gta gag tgg cta cgg cca atg att cgc gat ccc gat gct ctc gtg   672
Arg Val Glu Trp Leu Arg Pro Met Ile Arg Asp Pro Asp Ala Leu Val
    210                 215                 220
```

```
cgt gct gaa act gcg ttg gcg ttg gga aaa tca ggc gat gag agt gca        720
Arg Ala Glu Thr Ala Leu Ala Leu Gly Lys Ser Gly Asp Glu Ser Ala
225                 230                 235                 240 gtt gag cag ctc gtg tcc atg gtt ctc acc ggt ctt cgg gac gtg gag        768
Val Glu Gln Leu Val Ser Met Val Leu Thr Gly Leu Arg Asp Val Glu
                245                 250                 255 gca gcc gaa ttg ctt gcc gga ttt ggg gag ccc gtg cag tta gat gtg        816
Ala Ala Glu Leu Leu Ala Gly Phe Gly Glu Pro Val Gln Leu Asp Val
            260                 265                 270 ttc aag aaa ttt gcg cgg acg ctg gat gat gag gaa aca atg tcc ccg        864
Phe Lys Lys Phe Ala Arg Thr Leu Asp Asp Glu Glu Thr Met Ser Pro
        275                 280                 285 acg cgt ggt cgg att gcg caa gcg ttg gcg gag ttt aat ctt gcg cct        912
Thr Arg Gly Arg Ile Ala Gln Ala Leu Ala Glu Phe Asn Leu Ala Pro
    290                 295                 300 gtg gcg ttt ttg gtt gag cag cta gtt gat gat gac aat ccg acg gtt        960
Val Ala Phe Leu Val Glu Gln Leu Val Asp Asp Asp Asn Pro Thr Val
305                 310                 315                 320 gct ttt act gcg gct gcg att atc aaa gcc aag ggg ctg aag taa          1005
Ala Phe Thr Ala Ala Ala Ile Ile Lys Ala Lys Gly Leu Lys
                325                 330

<210> SEQ ID NO 4
<211> LENGTH: 334
<212> TYPE: PRT
<213> ORGANISM: Corynebacterium glutamicum

<400> SEQUENCE: 4

Met Leu Ile Gly Glu Val Ser Lys Leu Ser Gly Val Ser Ala Arg Met
1               5                   10                  15

Leu Arg His Tyr Glu Lys Leu Gly Leu Val Glu Pro Lys Gln Ser Thr
            20                  25                  30

Ala Gly Tyr Arg Glu Tyr Ser Glu Gly Asp Val Arg Arg Ile Phe His
        35                  40                  45

Ile Glu Gly Leu Arg Ser Leu Gly Leu Ser Leu Lys Gln Val Gly Asp
    50                  55                  60

Ala Leu Glu Asp Pro Asp Phe Asp Pro Gln Ala Val Ile Ser Glu Met
65                  70                  75                  80

Ile Ala Glu Thr Ser Ala Arg Ile Ser Met Glu Arg Glu Leu Leu Ala
                85                  90                  95

Arg Leu Lys Ala Val Arg His Ala Gln Ala Ser Asp Trp Glu Ser Ala
            100                 105                 110

Leu Asp Ala Val Gln Ile Leu Arg Arg Leu Arg Ser Gly Asp Pro Ala
        115                 120                 125

Gln Arg Gln Ala Val Ala Tyr Asp Ser Val Ser Gly Lys Glu Ala Val
    130                 135                 140

Ala Leu Glu Thr Leu Val Glu Ser Ala Leu Gly Glu Ser His Leu Asn
145                 150                 155                 160

Ala Glu Gly Ala Leu Ser Trp Ala Val Gln Arg Gly Glu Glu Ala
                165                 170                 175

Val Ala Leu Ala Ala Arg Gly Leu Arg Ser Arg Asp Ala Ala Val Arg
            180                 185                 190

Leu Arg Ala Val Arg Ile Val Ala Ser Ala Pro Ser Ala Val Ala Asp
        195                 200                 205

Arg Val Glu Trp Leu Arg Pro Met Ile Arg Asp Pro Asp Ala Leu Val
    210                 215                 220
```

```
Arg Ala Glu Thr Ala Leu Ala Leu Gly Lys Ser Gly Asp Glu Ser Ala
225                 230                 235                 240

Val Glu Gln Leu Val Ser Met Val Leu Thr Gly Leu Arg Asp Val Glu
            245                 250                 255

Ala Ala Glu Leu Leu Ala Gly Phe Gly Glu Pro Val Gln Leu Asp Val
            260                 265                 270

Phe Lys Lys Phe Ala Arg Thr Leu Asp Asp Glu Glu Thr Met Ser Pro
        275                 280                 285

Thr Arg Gly Arg Ile Ala Gln Ala Leu Ala Glu Phe Asn Leu Ala Pro
    290                 295                 300

Val Ala Phe Leu Val Glu Gln Leu Val Asp Asp Asp Asn Pro Thr Val
305                 310                 315                 320

Ala Phe Thr Ala Ala Ala Ile Ile Lys Ala Lys Gly Leu Lys
                325                 330

<210> SEQ ID NO 5
<211> LENGTH: 861
<212> TYPE: DNA
<213> ORGANISM: Corynebacterium glutamicum
<220> FEATURE:
<221> NAME/KEY: CDS
<222> LOCATION: (1)..(861)

<400> SEQUENCE: 5 gtg aat gat gct ggc ttg aag acg cga aac ccg gtg ctt gcc ccc att      48
Val Asn Asp Ala Gly Leu Lys Thr Arg Asn Pro Val Leu Ala Pro Ile
1               5                   10                  15 ttg atg gtg gtt aac ggc gtg tcc ctt tat gcc gga gca gcg ttg gcg      96
Leu Met Val Val Asn Gly Val Ser Leu Tyr Ala Gly Ala Ala Leu Ala
            20                  25                  30 gtg ggg ctg ttt gag agt ttc cca ccc gcg ttg gtt gcg tgg atg cga     144
Val Gly Leu Phe Glu Ser Phe Pro Pro Ala Leu Val Ala Trp Met Arg
        35                  40                  45 gta gca gcg gct gcg gtg att ttg ctt gtg ctg tat cgg cct gca gtg     192
Val Ala Ala Ala Ala Val Ile Leu Leu Val Leu Tyr Arg Pro Ala Val
    50                  55                  60 cga aat ttt att ggg cag acc ggg ttt tat gcg gcg gtg tat ggc gtt     240
Arg Asn Phe Ile Gly Gln Thr Gly Phe Tyr Ala Ala Val Tyr Gly Val
65                  70                  75                  80 tcc acg ctt gcc atg aac atc acg ttc tat gag gcg atc gcc cgc att     288
Ser Thr Leu Ala Met Asn Ile Thr Phe Tyr Glu Ala Ile Ala Arg Ile
                85                  90                  95 ccg atg ggt acc gcg gtg gcc att gag ttc ttg gga cct att gca gtg     336
Pro Met Gly Thr Ala Val Ala Ile Glu Phe Leu Gly Pro Ile Ala Val
            100                 105                 110 gcc gcg ttg ggc agt aag acg ctg cgg gat tgg gct gcg ttg gtt tta     384
Ala Ala Leu Gly Ser Lys Thr Leu Arg Asp Trp Ala Ala Leu Val Leu
        115                 120                 125 gct ggc atc gga gtg ata att att agc ggt gcg cag tgg tcg gcc aac     432
Ala Gly Ile Gly Val Ile Ile Ile Ser Gly Ala Gln Trp Ser Ala Asn
    130                 135                 140 agc gtg ggc gtc atg ttt gca ctg gca gca gca tta ctg tgg gct gcg     480
Ser Val Gly Val Met Phe Ala Leu Ala Ala Ala Leu Leu Trp Ala Ala
145                 150                 155                 160 tac atc atc gcg gga aac cgc att gca ggc gat gcc tca agt aga         528
Tyr Ile Ile Ala Gly Asn Arg Ile Ala Gly Asp Ala Ser Ser Arg
                165                 170                 175 acc ggc atg gcg gtg gga ttc acg tgg gca tca gtg ttg tct ttg ccg     576
Thr Gly Met Ala Val Gly Phe Thr Trp Ala Ser Val Leu Ser Leu Pro
            180                 185                 190
```

```
ttg gcg atc tgg tgg tgg ccg ggt ctg gga gca acg gaa ctt acg tta    624
Leu Ala Ile Trp Trp Trp Pro Gly Leu Gly Ala Thr Glu Leu Thr Leu
        195                 200                 205 atc gag gtc atc gga tta gca ctt ggt ttg ggc gtg ctg tcg gcg gtg    672
Ile Glu Val Ile Gly Leu Ala Leu Gly Leu Gly Val Leu Ser Ala Val
    210                 215                 220 att cct tat ggc ctt gac cag att gtg ctc cgc atg gcc ggg cga tcc    720
Ile Pro Tyr Gly Leu Asp Gln Ile Val Leu Arg Met Ala Gly Arg Ser
225                 230                 235                 240 tac ttt gcg ctg ctc ctg gct att ttg ccg atc agc gcc gcg ctc atg    768
Tyr Phe Ala Leu Leu Leu Ala Ile Leu Pro Ile Ser Ala Ala Leu Met
                245                 250                 255 gga gcg ctt gcg ctg ggc caa atg ttg tcg gtg gct gag ctt gtc ggc    816
Gly Ala Leu Ala Leu Gly Gln Met Leu Ser Val Ala Glu Leu Val Gly
            260                 265                 270 att gtg ctg gtt gtc atc gca gtt gct ttg cga cgc ccc tcc tag        861
Ile Val Leu Val Val Ile Ala Val Ala Leu Arg Arg Pro Ser
        275                 280                 285
```

<210> SEQ ID NO 6
<211> LENGTH: 286
<212> TYPE: PRT
<213> ORGANISM: Corynebacterium glutamicum

<400> SEQUENCE: 6

```
Val Asn Asp Ala Gly Leu Lys Thr Arg Asn Pro Val Leu Ala Pro Ile
1               5                   10                  15

Leu Met Val Val Asn Gly Val Ser Leu Tyr Ala Gly Ala Ala Leu Ala
            20                  25                  30

Val Gly Leu Phe Glu Ser Phe Pro Pro Ala Leu Val Ala Trp Met Arg
        35                  40                  45

Val Ala Ala Ala Val Ile Leu Leu Val Leu Tyr Arg Pro Ala Val
    50                  55                  60

Arg Asn Phe Ile Gly Gln Thr Gly Phe Tyr Ala Ala Val Tyr Gly Val
65                  70                  75                  80

Ser Thr Leu Ala Met Asn Ile Thr Phe Tyr Glu Ala Ile Ala Arg Ile
                85                  90                  95

Pro Met Gly Thr Ala Val Ala Ile Glu Phe Leu Gly Pro Ile Ala Val
            100                 105                 110

Ala Ala Leu Gly Ser Lys Thr Leu Arg Asp Trp Ala Ala Leu Val Leu
        115                 120                 125

Ala Gly Ile Gly Val Ile Ile Ser Gly Ala Gln Trp Ser Ala Asn
    130                 135                 140

Ser Val Gly Val Met Phe Ala Leu Ala Ala Leu Leu Trp Ala Ala
145                 150                 155                 160

Tyr Ile Ile Ala Gly Asn Arg Ile Ala Gly Asp Ala Ser Ser Ser Arg
                165                 170                 175

Thr Gly Met Ala Val Gly Phe Thr Trp Ala Ser Val Leu Ser Leu Pro
            180                 185                 190

Leu Ala Ile Trp Trp Trp Pro Gly Leu Gly Ala Thr Glu Leu Thr Leu
        195                 200                 205

Ile Glu Val Ile Gly Leu Ala Leu Gly Leu Gly Val Leu Ser Ala Val
    210                 215                 220

Ile Pro Tyr Gly Leu Asp Gln Ile Val Leu Arg Met Ala Gly Arg Ser
225                 230                 235                 240
```

```
Tyr Phe Ala Leu Leu Leu Ala Ile Leu Pro Ile Ser Ala Ala Leu Met
                245                 250                 255

Gly Ala Leu Ala Leu Gly Gln Met Leu Ser Val Ala Glu Leu Val Gly
            260                 265                 270

Ile Val Leu Val Val Ile Ala Val Ala Leu Arg Arg Pro Ser
        275                 280                 285

<210> SEQ ID NO 7
<211> LENGTH: 20
<212> TYPE: DNA
<213> ORGANISM: artificial sequence
<220> FEATURE:
<223> OTHER INFORMATION: primer NC2067F

<400> SEQUENCE: 7
acgagggtga attcaccgag                                             20

<210> SEQ ID NO 8
<211> LENGTH: 42
<212> TYPE: DNA
<213> ORGANISM: artificial sequence
<220> FEATURE:
<223> OTHER INFORMATION: primer NC2067R1

<400> SEQUENCE: 8
ccacgcgccg cgcttcctcc agcatggcac ttatgttcat gg                    42

<210> SEQ ID NO 9
<211> LENGTH: 20
<212> TYPE: DNA
<213> ORGANISM: artificial sequence
<220> FEATURE:
<223> OTHER INFORMATION: primer NC2067F1

<400> SEQUENCE: 9
ctggaggaag cgcggcgcgt                                             20

<210> SEQ ID NO 10
<211> LENGTH: 21
<212> TYPE: DNA
<213> ORGANISM: artificial sequence
<220> FEATURE:
<223> OTHER INFORMATION: primer NC2067R

<400> SEQUENCE: 10
gcgccggatc ccccgatcgc a                                           21

<210> SEQ ID NO 11
<211> LENGTH: 30
<212> TYPE: DNA
<213> ORGANISM: artificial sequence
<220> FEATURE:
<223> OTHER INFORMATION: primer NC2067-SmF

<400> SEQUENCE: 11
tgattccccc gggcagatcg acggcgtgga                                  30

<210> SEQ ID NO 12
<211> LENGTH: 32
<212> TYPE: DNA
<213> ORGANISM: artificial sequence
<220> FEATURE:
<223> OTHER INFORMATION: primer NC2067-SmR

<400> SEQUENCE: 12
```

```
cccaatcccg ggcctgcgca tgacgcaccg ct                                    32

<210> SEQ ID NO 13
<211> LENGTH: 18
<212> TYPE: DNA
<213> ORGANISM: artificial sequence
<220> FEATURE:
<223> OTHER INFORMATION: primer P1

<400> SEQUENCE: 13
gcagatcgac ggcgtgga                                                    18

<210> SEQ ID NO 14
<211> LENGTH: 20
<212> TYPE: DNA
<213> ORGANISM: artificial sequence
<220> FEATURE:
<223> OTHER INFORMATION: primer P2

<400> SEQUENCE: 14
cctgcgcatg acgcaccgct                                                  20

<210> SEQ ID NO 15
<211> LENGTH: 21
<212> TYPE: DNA
<213> ORGANISM: artificial sequence
<220> FEATURE:
<223> OTHER INFORMATION: primer NC2066F

<400> SEQUENCE: 15
acccgcatgc cagttgatga c                                                21

<210> SEQ ID NO 16
<211> LENGTH: 40
<212> TYPE: DNA
<213> ORGANISM: artificial sequence
<220> FEATURE:
<223> OTHER INFORMATION: primer NC2066R1

<400> SEQUENCE: 16
cattcacatc acgacacctt accccactga gcttggacac                            40

<210> SEQ ID NO 17
<211> LENGTH: 22
<212> TYPE: DNA
<213> ORGANISM: artificial sequence
<220> FEATURE:
<223> OTHER INFORMATION: primer NC2066F1

<400> SEQUENCE: 17
aaggtgtcgt gatgtgaatg at                                               22

<210> SEQ ID NO 18
<211> LENGTH: 20
<212> TYPE: DNA
<213> ORGANISM: artificial sequence
<220> FEATURE:
<223> OTHER INFORMATION: primer NC2066R

<400> SEQUENCE: 18
caagtgctaa tccgatgacc                                                  20

<210> SEQ ID NO 19
<211> LENGTH: 34
<212> TYPE: DNA
<213> ORGANISM: artificial sequence
```

```
<220> FEATURE:
<223> OTHER INFORMATION: primer NC2066-SmF

<400> SEQUENCE: 19
gaggtacccg ggcgaccatt cggtgcaagt caag                              34

<210> SEQ ID NO 20
<211> LENGTH: 37
<212> TYPE: DNA
<213> ORGANISM: artificial sequence
<220> FEATURE:
<223> OTHER INFORMATION: primer NC2066-SmR

<400> SEQUENCE: 20
tgctcccagc ccgggccacc accagatcgc caacggc                           37
```